United States Patent [19]

Wang et al.

[11] Patent Number: 4,985,429
[45] Date of Patent: Jan. 15, 1991

[54] AMINOMETHYL OXOOXAZOLIDINYL CYCLOALKYLBENZENE DERIVATIVES USEFUL AS ANTIBACTERIAL AGENTS

[75] Inventors: Chia-Lin J. Wang; Mark A. Wuonola, both of Wilmington, Del.

[73] Assignee: E. I. du Pont de Nemours and Company, Wilmington, Del.

[21] Appl. No.: 497,211

[22] Filed: Mar. 15, 1990

Related U.S. Application Data

[62] Division of Ser. No. 233,828, Aug. 19, 1988, Pat. No. 4,921,869, which is a division of Ser. No. 106,358, Oct. 9, 1987, Pat. No. 4,801,600.

[51] Int. Cl.$^5$ .................. A61K 31/495; C07D 405/14; C07D 413/14
[52] U.S. Cl. .................... 514/253; 514/376; 544/369; 548/229; 548/231; 548/232; 548/234; 549/399; 549/401; 549/402; 549/466
[58] Field of Search .................. 544/369; 514/253

[56] References Cited

U.S. PATENT DOCUMENTS

| | | | |
|---|---|---|---|
| Re. 29,607 | 4/1978 | Fauran et al. | 548/232 |
| 3,687,965 | 8/1972 | Fauran et al. | 548/229 |
| 4,128,654 | 12/1978 | Fugitt et al. | 514/376 |
| 4,250,318 | 2/1981 | Dostert et al. | 548/229 |
| 4,340,606 | 7/1982 | Fugitt et al. | 514/376 |
| 4,461,773 | 7/1984 | Gregory | 514/376 |
| 4,476,136 | 10/1984 | Dostert | 548/229 |
| 4,705,799 | 11/1987 | Gregory | 548/229 |
| 4,801,600 | 1/1989 | Wang et al. | 514/376 |
| 4,921,869 | 5/1990 | Wang et al. | 514/376 |

FOREIGN PATENT DOCUMENTS

| | | | |
|---|---|---|---|
| 127902 | 12/1984 | European Pat. Off. | |
| 184170 | 6/1986 | European Pat. Off. | |
| 1222708 | 2/1972 | United Kingdom | 548/229 |
| 2076813 | 6/1980 | United Kingdom | 548/229 |
| 2094299 | 9/1982 | United Kingdom | |

*Primary Examiner*—Cecilia Shen

[57] ABSTRACT

Aminomethyl oxooxazolidinyl cycloalkylbenzene derivatives, such as l-N-[3-(2,3-dihydro-1-oxo-1H-inden-5-yl)-2-oxooxazolidin-5-ylmethyl]acetamide, possess useful antibacterial activity.

18 Claims, No Drawings

AMINOMETHYL OXOOXAZOLIDINYL CYCLOALKYLBENZENE DERIVATIVES USEFUL AS ANTIBACTERIAL AGENTS

This is a division of application Ser. No. 07/233,828, filed Aug. 19, 1988 now U.S. Pat. No. 4,921,869 which is a divisional of Ser. No. 07/106,358 filed Oct. 9, 1987 now U.S. Pat. No. 4,801,600.

TECHNICAL FIELD

This invention relates to novel aminomethyl oxooxazolidinyl cycloalkylbenzene derivatives, their preparation, to pharmaceutical compositions containing them, and to methods of using them to alleviate bacterial infections.

BACKGROUND OF THE INVENTION

At the present time, no existing antibacterial product provides all features deemed advantageous. There is continual development of resistance by bacterial strains. A reduction of allergic reactions and of irritation at the site of injection, and greater biological half-life (i.e., longer in vivo activity) are currently desirable features for antibacterial products.

U.S. Pat. No. 4,128,654 issued to Fugitt et al. on Dec. 5, 1978, discloses, among others, compounds of the formula:

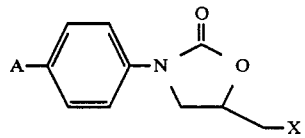

where
A=RS(O)$_n$;
X=Cl, Br or F;
R=C$_1$-C$_3$ alkyl; and
n=0, 1 or 2.

The compounds are disclosed as being useful in controlling fungal and bacterial diseases of plants.

U.S. Reissue Pat. No. 29,607 reissued Apr. 11, 1978 discloses derivatives of 5-hydroxymethyl-3-substituted-2-oxazolidinones of the formula:

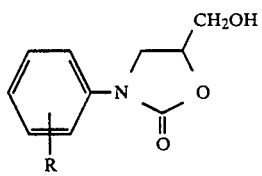

where R is H, F, CH$_3$, or CF$_3$. Such compounds are described as having antidepressive, tranquilizing, sedative, and antiinflammatory properties.

U.S. Pat. No. 4,250,318, which was issued on Feb. 10, 1981, discloses antidepressant compounds of the formula:

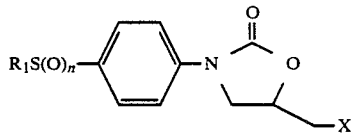

where R' can be, among others, a para-n-pentylamino group, an SR$_1$ group where R$_1$ is C$_1$-C$_5$ alkyl, or an acetylmethylthio group.

U.S. Pat. No. 4,340,606 issued to Fugitt et al. on July 20, 1982, discloses antibacterial agents of the general formula:

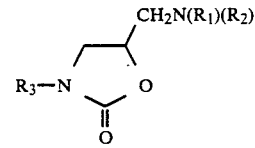

where
R$_1$=CH$_3$, C$_2$H$_5$, CF$_2$H, CF$_3$ or CF$_2$CF$_2$H; and
X=OR$_2$ (R$_2$=H or various acyl moieties).

U.S. Pat. No. 3,687,965, issued to Fauran et al. on Aug. 29, 1972, discloses compounds of the formula:

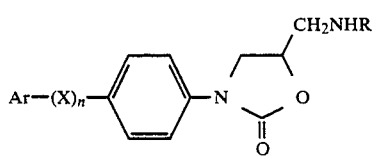

where
—N(R$_1$)(R$_2$) represents either dialkylamino radical in which the alkyl portions have one to five carbon atoms, or a heterocyclic amino radical which may be substituted by an alkyl radical having one to five carbon atoms or by a pyrrolidinocarbonylmethyl radical, and R$_3$ represents a phenyl radical which may be substituted by one or more of the following radicals:
an alkoxy radical having one to five carbon atoms;
a halogen atom;
a trifluoromethyl radical, or
a carboxyl radical which may be esterified.

The patent states that these compounds possess hypotensive, vasodilatatory, spasmolytic, sedative, myorelaxant, analgesic and antiinflammatory properties. There is no mention of antibacterial properties.

Belgian Patent No. 892,270, published Aug. 25, 1982, discloses monoamine oxidase inhibitors of the formula

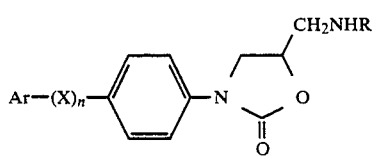

where
R is H, C$_1$-C$_4$ alkyl or propargyl;
Ar is phenyl, optionally substituted by halo or trifluoromethyl;
n is 0 or 1; and
X is —CH$_2$CH$_2$—, —CH=CH—, an acetylene group or —CH$_2$O—.

U.S. Pat. No. 4,461,773 issued to W. A. Gregory on July 24, 1984, discloses antibacterial agents of the formula

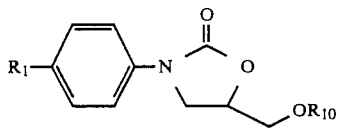

wherein, for the l, and mixtures of the d and l stereoisomers of the compound, $R_1$ is $R_2SO_2$,

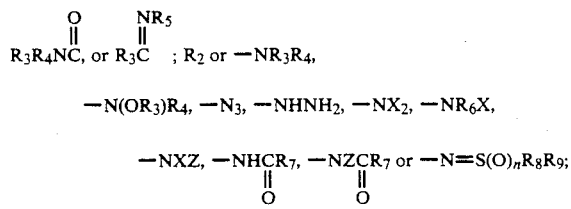

$R_3$ and $R_4$ are independently H, alkyl of 1–4 carbons or cycloalkyl of 3–8 carbons;

$R_5$ is $NR_3R_4$ or $OR_3$;

$R_6$ is alkyl of 1–4 carbons;

$R_7$ is alkyl of 1–4 carbons, optionally substituted with one or more halogens;

$R_8$ and $R_9$ are independently alkyl of 1–4 carbons or, taken together are —$(CH_2)_p$—;

$R_{10}$ is H, alkyl of 1–3 carbons, —$CR_{11}$,

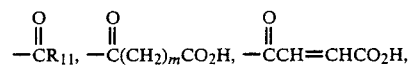

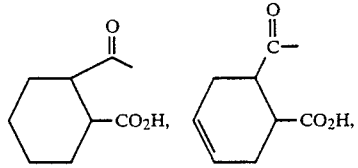

$R_{11}$ is alkyl of 1–12 carbons;

$R_{12}$ is H, alkyl of 1–5 carbons, $CH_2OH$ or $CH_2SH$;

X is Cl, Br or I;

Z is a physiologically acceptable cation;

m is 2 or 3;

n is 0 or 1; and p is 3, 4 or 5;

and when $R_{10}$ is alkyl of 1–3 carbons, $R_1$ can also be $CH_3S(O)_q$ where q is 0, 1 or 2;

or a pharmaceutically acceptable salt thereof.

European Patent Application Nos. 127,902, published Dec. 12, 1984, and 184,170, published June 11, 1986, disclose antibacterial agents of the formula:

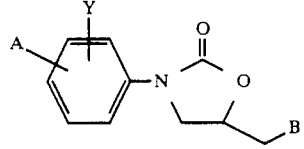

wherein, for the l, and mixtures of the d and l stereoisomers of the compound,

A is —$NO_2$, —$S(O)_nR_1$, —$S(O)_2$—$N$=$S(O)_pR_2R_3$, —SH,

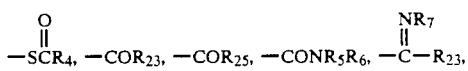

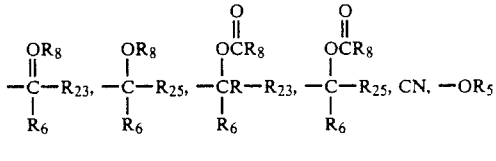

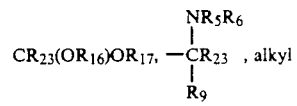

of 1 to 8 carbons, optionally substituted with one or more halogen atoms, OH, =O other than at alpha position, $S(O)_nR_{24}$, $NR_5R_6$, alkenyl of 2–5 carbons, alkynyl of 2–5 carbons or cycloalkyl of 3–8 carbons;

$R_1$ is $C_1$–$C_4$ alkyl, optionally substituted with one or more halogen atoms, OH, CN, $NR_5R_6$ or $CO_2R_8$; $C_2$–$C_4$ alkenyl;

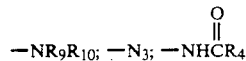

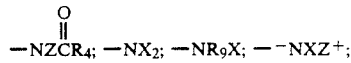

$R_2$ and $R_3$ are independently $C_1$–$C_2$ alkyl or, taken together are —$(CH_2)_q$—;

$R_4$ is alkyl of 1–4 carbons, optionally substituted with one or more halogens;

$R_5$ and $R_6$ are independently H, alkyl of 1–4 carbons or cycloalkyl of 3–8 carbons;

$R_7$ is —$NR_5R_6$, —$OR_5$ or

$R_8$ is H or alkyl of 1–4 carbons;

$R_9$ is H, $C_1$–$C_4$ alkyl or $C_3$–$C_8$ cycloalkyl;

$R_{10}$ is H, $C_1$–$C_4$ alkyl, $C_2$–$C_4$ alkenyl, $C_3$–$C_4$ cycloalkyl, —$OR_8$ or —$NR_{11}R_{11A}$;

$R_{11}$ and $R_{11A}$ are independently H or $C_1$–$C_4$ alkyl, or taken together, are —$(CH_2)_r$—;

X is Cl, Br or I;

Y is H, F, Cl, Br, alkyl or 1–3 carbons, or $NO_2$, or A and Y taken together can be —O—$(CH_2)_tO$—;

Z is a physiologically acceptable cation;

n is 0, 1 or 2;
p is 0 or 1;
q is 3, 4 or 5;
r is 4 or 5;
t is 1, 2 or 3;
B is —NH$_2$,

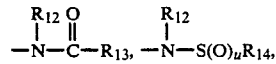

or N$_3$;

R$_{12}$ is H, C$_1$-C$_{10}$ alkyl or C$_3$-C$_8$ cycloalkyl;

R$_{13}$ is H; C$_1$-C$_4$ alkyl optionally substituted with one or more halogen atoms; C$_2$-C$_4$ alkenyl; C$_3$-C$_4$ cycloalkyl; phenyl;

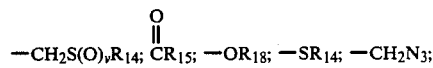

the aminoalkyl groups derived from α-amino acids such as glycine, L-alanine, L-cysteine, L-proline, and D-alanine; —NR$_{19}$R$_{20}$; or C(NH$_2$)R$_{21}$R$_{22}$;

R$_{14}$ is C$_1$-C$_4$ alkyl, optionally substituted with one or more halogen atoms;

R$_{15}$ is H or C$_1$-C$_4$ alkyl, optionally substituted with one or more halogen atoms;

R$_{16}$ and R$_{17}$ are independently C$_1$-C$_4$ alkyl or, taken together, are —(CH$_2$)$_m$—;

R$_{18}$ is C$_1$-C$_4$ alkyl or C$_7$-C$_{11}$ aralkyl;

R$_{19}$ and R$_{20}$ are independently H or C$_1$-C$_2$ alkyl;

R$_{21}$ and R$_{22}$ are independently H, C$_1$-C$_4$ alkyl, C$_3$-C$_6$ cycloalkyl, phenyl or, taken together, are —(CH$_2$)$_s$—;

u is 1 or 2;
v is 0, 1 or 2;
m is 2 or 3;
s is 2, 3, 4 or 5; and

R$_{23}$ is H, alkyl of 1-8 carbons optionally substituted with one or more halogens, or cycloalkyl of 3-8 carbons;

R$_{24}$ is alkyl of 1-4 carbons or cycloalkyl of 3-8 carbons;

R$_{25}$ is alkyl of 1-4 carbons substituted with one or more of —S(O)$_n$R$_{24}$,

or alkenyl of 2-5 carbons optionally substituted with CHO; or a pharmaceutically suitable salt thereof; provided that:

(1) when A is CH$_3$S—, then B is not

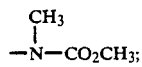

(2) when A is CH$_3$SO$_2$—, then B is not

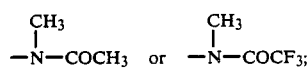

(3) when A is H$_2$NSO$_2$— and B is

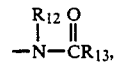

then R$_{12}$ is H;

(4) when A is —CN, B is not —N$_3$;
(5) when A is (CH$_3$)$_2$CH, B is not NHCOCH$_2$Cl;
(6) when A is OR$_5$, then B is not NH$_2$;
(7) when A is F, then B is not NHCO$_2$CH$_3$.

None of the above-mentioned references suggest the novel antibacterial compounds of this invention.

SUMMARY OF THE INVENTION

According to the present invention, there is provided an oxazolidinone having the formula:

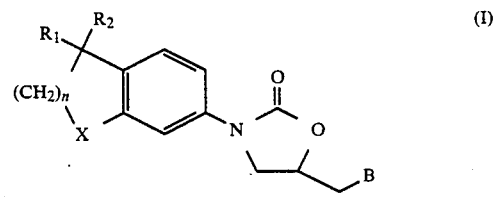

wherein for the l isomer or racemic mixtures containing it
B is NH$_2$,

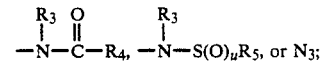

u is 1 or 2;
R$_3$ is H, alkyl of 1-10 carbon atoms, or cycloalkyl of 3-8 carbon atoms;
R$_4$ is H, alkyl of 1-4 carbon atoms, alkenyl of 2-4 carbon atoms, cycloalkyl of 3-4 carbon atoms, or OR$_5$;
R$_5$ is alkyl of 1-4 carbon atoms;
X is CH$_2$, O, S, or NR$_6$;
R$_6$ is H or alkyl of 1-4 carbon atoms;
n is 1-3; and
R$_1$ and R$_2$ taken together are H$_2$, H and OH, =O, H and N(R$_6$)$_2$, =NOH, =NOR$_5$, =NOCR$_4$, or =N—N⟨piperazine⟩N—CH$_3$;

or a pharmaceutically suitable salt thereof; provided that:
(1) when n is 2, then X is not S; and
(2) when n is 3, then X is not O or NR$_6$.

Also provided is a process for preparing compounds of Formula (I), such a process being described in detail hereinafter.

Additionally provided are a pharmaceutical composition containing a compound of Formula (I) and a method of using a compound of Formula (I) to treat a bacterial infection in a mammal.

PREFERRED EMBODIMENTS

Preferred compounds are the oxazolidinones of Formula (I) wherein:
(a) B is

where R₄ is H, CH₃, or OR₅; or (b) R₁ and R₂ taken together are

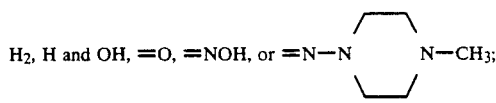

or (c) n is 1-2; or
(d) X is CH₂.

More preferred compounds are the oxazolidinones of Formula (I) wherein:

(a) B is

or (b) R₁ and R₂ taken together are

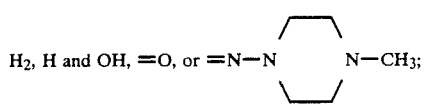

or (c) n is 1; or
(d) X is CH₂.

Specifically preferred are the following compounds:

(l)-N-[3-(2,3-dihydro-1-oxo-1H-inden-5-yl)-2-oxooxazolidin-5-ylmethyl]acetamide;

(l)-N-[3-(2,3-dihydro-1H-inden-5-yl)-2-oxooxazolidin-5-ylmethyl]acetamide;

(l)-N-[3-(2,3-dihydro-1-hydroxy-1H-inden-5-yl)-2-oxooxazolidin-5-ylmethyl]acetamide.

DETAILED DESCRIPTION

The compounds of Formula (I) contain at least one chiral center and, as such, exist as two individual isomers or as a mixture of both. This invention relates to the levorotatory isomer (l), which for many of the compounds in this invention can be referred to as the (S) isomer, as well as mixtures containing both the (R) and (S) isomers. Additional chiral centers may be present in the B group, or when R₁ and R₂ taken together are H and OH or H and N(R₆)₂. The invention relates to all possible stereoisomers of the above.

For the purposes of this invention, the l-isomer of compounds of Formula (I) is intended to mean compounds of the configuration depicted; when B is NHAc, and closely related groups, this isomer is described as the (S)-isomer in the Cahn-Ingold-Prelog nomenclature:

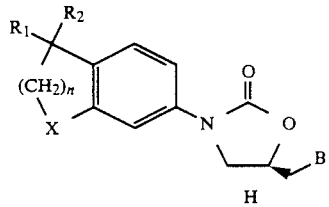

Synthesis

Compounds of Formula (I) where R₁ and R₂ taken together are H₂, and X and n are as previously defined, can be prepared as follows:

Scheme 1

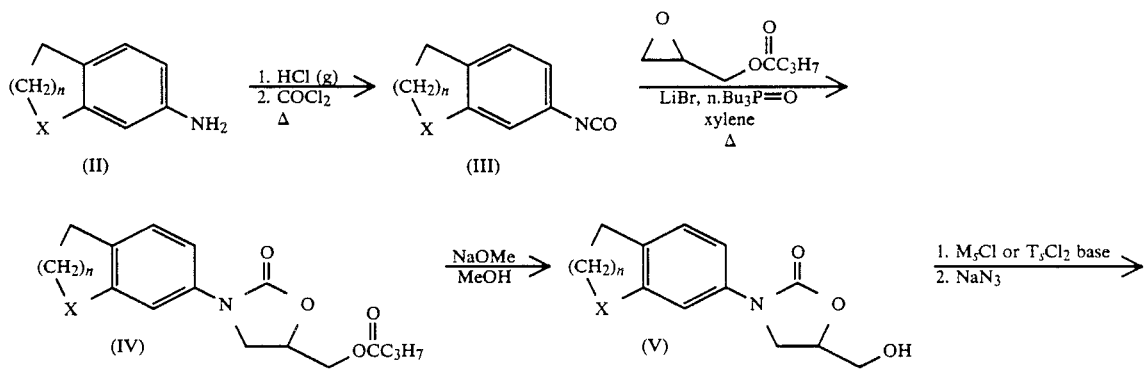

-continued
Scheme 1

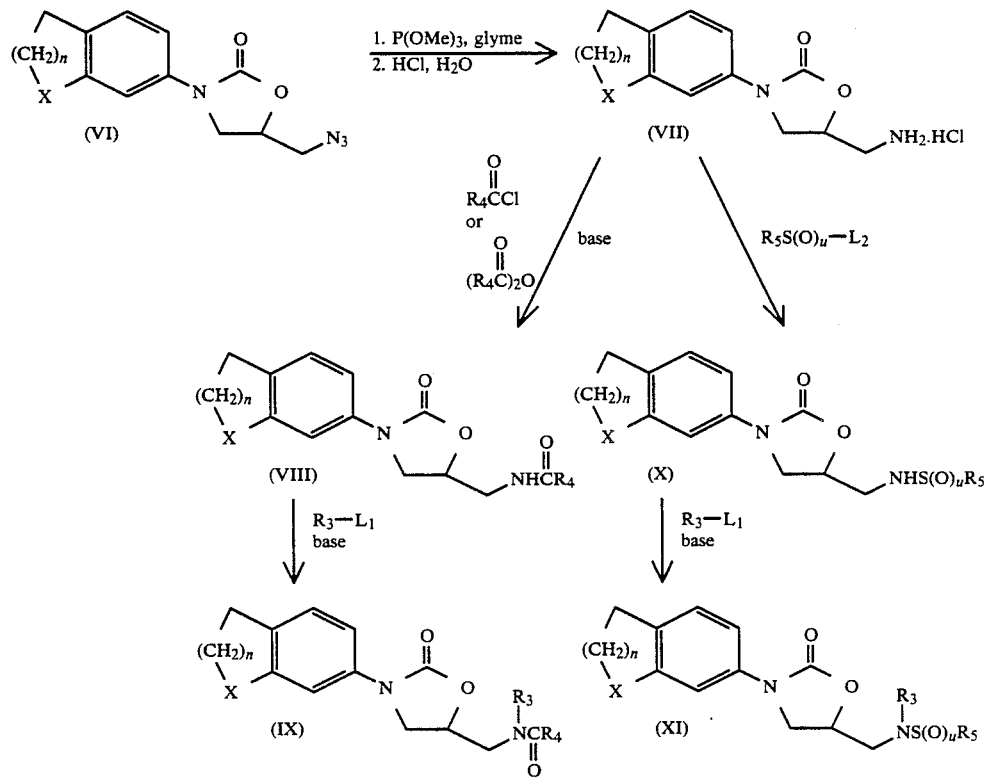

Compounds of Formula (II) are converted to isocyanates (III) by treatment of their hydrochloride salts with phosgene in a refluxing solvent such as xylene. Other solvents such as benzene or toluene may be used. Isocyanates (III) react with glycidyl butyrate in the presence of lithium bromide and tributylphosphine oxide in refluxing xylene or toluene to afford oxazolidinones (IV). Compounds (IV), upon treatment with sodium methoxide in methanol or sodium ethoxide in ethanol at 0° C. to room temperature give alcohols (V). Then alcohols (V) can be converted to compounds (VI)–(XI) by the process previously described in published European applications Nos. 127,902 and 184,170. $L_1$ is a leaving group which can be Cl, Br, I, OMs or OTs. $L_2$ is also a leaving group and can be Cl, Br, or I.

Glycidyl butyrate can be resolved by procedures described in W. E. Ladner and G. M. Whitesides, *J. Am. Chem. Soc.*, 106, 7250 (1984). By using (R)-glycidyl butyrate in the synthesis, l-isomer of compounds of Formula (I) can be prepared.

Compounds of Formula (I) where $R_1$ and $R_2$ taken together are not $H_2$ but as described previously can be prepared as follows:

Scheme 2

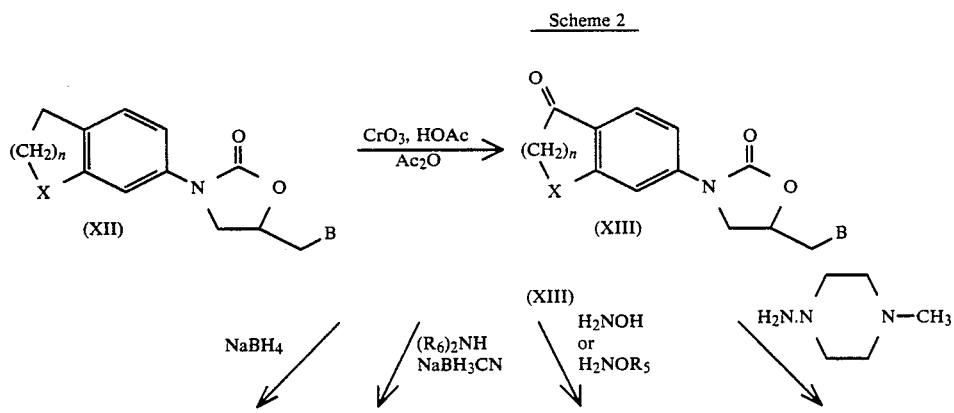

-continued
Scheme 2

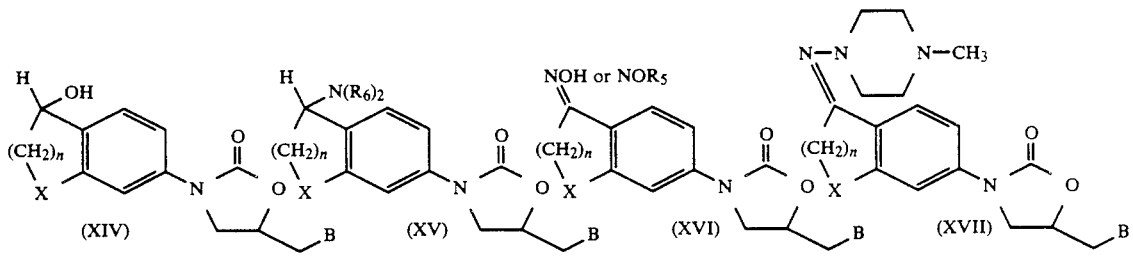

Oxidation of compounds of Formula (XII) with chromium (VI) oxide in acetic acid and acetic anhydride at room temperature affords ketones (XIII). When X=S, the sulfur might be oxidized to sulfoxide or sulfone by the above reaction condition. However, they can be easily reduced back to sulfide by catalytic hydrogenation in an alcoholic solvent such as ethanol.

Ketones (XIII) can then be converted to compounds (XIV)–(XVII) by standard procedures. For example, an alkali metal borohydride such as sodium borohydride in a solvent such as methanol or ethanol at 0° C. to room temperature reduces the ketone to hydroxy group to give compounds (XIV). Reaction of (XIII) with $(R_6)_2NH$ in the presence of sodium cyanoborohydride in an alcoholic solvent such as methanol or ethanol at room temperature to 80° C. yields amines (XV). Treatment of (XIII) with hydroxyamine hydrochloride or $H_2NOR_5$ in the presence of a base such as pyridine or triethylamine in an alcoholic solvent such as methanol or ethanol at room temperature to 100° C. gives oximes (XVI). The preparation of (XVII) is described below in Example 18 by reacting (XIII) with 1-amino-4-methyl piperazine in a refluxing solvent such as tetrahydrofuran (THF) or dioxane containing boron trifluoride etherate.

Pharmaceutically suitable salts of compounds of Formula (I) can be prepared in a number of ways known in the art. When $R_1$, $R_2$, X or B contain a basic nitrogen, pharmaceutically salts include those resulting from treatment with acids such as acetic, hydrochloric, sulfuric, phosphoric, succinic, fumaric, ascorbic, and glutaric acid.

The invention can be further understood by the following examples in which parts and percentages are by weight unless indicated otherwise.

EXAMPLE 1

Preparation of
(l)-N-[3-(2,3-Dihydro-1H-inden-5-yl)-2-oxooxazolidin-5-ylmethyl]acetamide (I; $R_1=R_2=H$, X=CH$_2$, n=1, B=NHCOCH$_3$)

Part A: Preparation of 5-Isocyanateindan (III, X=CH$_2$, n=1)

HCl gas was bubbled through a solution of 5-aminoindan (20 g, 0.15 mol) in xylene (400 mL) for 30 minutes. The mixture was then brought to reflux and phosgene was bubbled through while refluxing. When reaction was complete, nitrogen was bubbled through while the reaction cooled. Xylene was removed in vacuo and the resulting isocyanate (III, X=CH$_2$, n=1) was directly submitted to the next reaction.

Part B: Preparation of
(l)-N-[3-(2,3-Dihydro-1H-inden-5-yl)-2-oxooxazolidin-5-ylmethyl]butyrate (IV, X=CH$_2$, n=1)

A solution of lithium bromide (0.78 g, 9 mmol) and tributylphosphine oxide (1.96 g, 9 mmol) in xylene (200 mL) was refluxed for one hour. The heat was removed and a solution of isocyanate (III, X=CH$_2$, n=1) from Part A and (R)-glycidyl butyrate (18.6 g, 0.13 mol) in xylene (75 mL) was added slowly. After refluxing for one hour, xylene was removed in vacuo, the residue was diluted with methylene chloride and washed with brine. The separated organic layer was dried (MgSO$_4$). Purification of the crude product by flash column chromatography gave 26 g (67%) of the title compound (IV, X=CH$_2$, n=1). IR (neat): 1752 cm$^{-1}$; NMR (CDCl$_3$) δ: 7.43 (S,1H), 7.18 (S,2H), 4.83 (m,1H), 4.33 (2dd,2H), 4.10 (t,1H), 3.80 (dd,1H), 2.88 (dd,4H), 2.33 (t,2H), 2.07 (p,2H), 1.60 (m,2H), 0.92 (t,3H); MS: m/z 303.1470 (M$^+$) calcd for C$_{17}$H$_{21}$NO$_4$, 303.1471; $[\alpha]_D = -42°$ (C=0.8, CHCl$_3$)

Part C: Preparation of
(l)-5-Hydroxymethyl-N-[3-(2,3-dihydro-1H-inden-5-yl)-2-oxooxazolidin] (V, X=CH$_2$, n=1)

Butyrate (IV, X=CH$_2$, n=1) (39 g, 0.13 mol) was treated with sodium methoxide (710 mg, 13 mmol) in methanol (500 mL) at room temperature for one hour. After removing methanol, the residue was taken up with 10% methanol-methylene chloride and the solid was filtered off. Removal of the solvent afforded 24.7 g (82%) of the title compound (V, X=CH$_2$, n=1) as a white solid, m.p. 209°–212° C.; NMR (CDCl$_3$) δ: 7.43 (s,1H), 7.20 (s,2H), 4.72 (m,1H), 3.99 (m,3H), 3.76 (m,1H), 2.87 (dd,4H), 2.68 (bs,1H,OH), 2.07 (p,2H).

Part D: Preparation of
(l)-5-Azidomethyl-N-[3-(2,3-dihydro-1H-inden-5-yl)-2-oxooxazolidin] (VI, X=CH$_2$, n=1)

To a solution of alcohol (V, X=CH$_2$, n=1) (23 g. 0.099 mol) in methylene chloride (300 mL) and triethylamine (28 mL) at 0° C. was added mesyl (Ms) chloride (22.5 g, 0.19 mol). The mixture was then stirred at room temperature for one hour. Additional mesyl chloride (6 g, 0.05 mol) and triethylamine (7.3 mL) were added and the reaction was continually stirred for two hours. It was washed with brine, the separated organic layer was dried (MgSO$_4$) and the solvent was evaporated to give 30.8 g of the mesylate which was dissolved in DMF (500 mL) and treated with sodium azide (12.9 g, 0.198 mol) at 85° C. for six hours. The reaction mixture was diluted with water and extracted with methylene chloride five times. The combined organic layer was washed with brine and dried (MgSO$_4$). Removal of the solvent in vacuo yielded 26 g (100%) of the title compound (VI, X=CH$_2$, n=1) as a solid. IR (nujol): 2101,1730 cm$^{-1}$; NMR (CDCl$_3$) δ: 7.42 (s,1H), 7.17 (s,2H), 4.73 (m,1H), 4.05 (t,1H), 3.80 (dd,1H), 3.63 (2dd,2H), 2.85 (dd,4H), 2.05 (p,2H); [α]$_D$=−122° (C=1, CH$_3$CN).

Part E: Preparation of (l)-5-Aminomethyl-N-[3-(2,3-dihydro-1H-inden-5-yl)-2-oxooxazolidin]hydrochloride (VII, X=CH$_2$, n=1)

To a solution of azide (VI, X=CH$_2$, n=1) (25 g, 0.097 mol) in glyme (400 mL) was added trimethylphosphite (14.9 mL, 0.13 mol) and the mixture was heated at 65° C. for one hour. Then 10 mL of 50% hydrochloric acid was added and the reaction was refluxed for eleven hours. Additional 15 mL of 50% hydrochloric acid was added and it was continually refluxed for 1.5 hours. Removal of the solvent in vacuo and the residue was washed with glyme followed by drying under high vacuum to afford 8.7 g (34%) of the title compound (VII, X=CH$_2$, n=1). m.p. >219° C. (dec).

Part F: Preparation of (l)-N-[3-(2,3-Dihydro-1H-inden-5-yl)-2-oxooxazolidin-5-ylmethyl]acetamide (I; R$_1$=R$_2$=H, X=CH$_2$, n=1, B=NHCOCH$_3$)

A solution of the hydrochloride salt (VII, X=CH$_2$, n=1) (8.7 g, 32 mmol) in THF-H$_2$O (30 mL - 5 mL) was neutralized with 2N sodium hydroxide aqueous solution. Then acetic anhydride (4.14 g, 41 mmol) was added. More sodium hydroxide solution was added to adjust pH to 6–7. Tetrahydrofuran was removed and the aqueous layer was extracted with chloroform three times. The chloroform layer was washed with brine and dried (MgSO$_4$). Removal of the solvent gave 8.8 g (100%) of (l)-N-[3-(2,3-dihydro-1H-inden-5-yl)-2-oxooxazolidin-5-ylmethyl]acetamide as a white solid. m.p. 131°–133° C.; IR (nujol): 1735, 1655 cm$^{-1}$; NMR (CDCl$_3$) δ: 7.37 (s,1H), 7.17 (s,2H), 6.47 (bs,1H), 4.73 (m,1H), 4.02 (t,1H), 3.78 (dd,1H), 3.63 (m,2H), 2.87 (dd,4H), 2.07 (p,2H), 2.00 (s,3H); MS: m/z 274.1310 (M$^+$), calcd. for C$_{15}$H$_{18}$N$_2$O$_3$, 274.1317; [α]$_D$=−31° (C=1, CH$_3$CN).

By using the procedures described in Example 1, the following compounds in Table I were prepared or can be prepared.

TABLE I

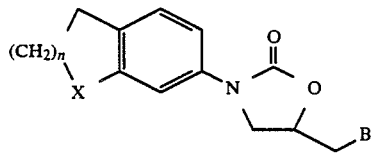

| Ex. | X | n | B | Isomer | m.p. (°C.) | [α]D |
|---|---|---|---|---|---|---|
| 1D | CH$_2$ | 1 | N$_3$ | l | | −122° (c = 1, CH$_3$CN) |
| 1E | CH$_2$ | 1 | NH$_2$ | l | >219 (dec, HCl salt) | |
| 1F | CH$_2$ | 1 | NHCOCH$_3$ | l | 131–133 | −31° (c = 1, CH$_3$CN) |
| 2 | CH$_2$ | 1 | NHCOCH$_3$ | dl | | |
| 3 | CH$_2$ | 1 | NHCOC$_2$H$_5$ | l | | |
| 4 | CH$_2$ | 2 | NHCOCH$_3$ | l | | |
| 5 | CH$_2$ | 3 | NHCOCH$_3$ | l | | |
| 6 | O | 1 | NHCO— | dl | | |
| 7 | O | 1 | NHCO$_2$CH$_3$ | l | | |
| 8 | O | 2 | NHSOCH$_3$ | l | | |
| 9 | O | 2 | N(CH$_3$)COCH$_3$ | l | | |
| 10 | S | 1 | NHCOCH$_3$ | l | | |
| 11 | S | 1 | NHSO$_2$CH$_3$ | l | | |
| 12 | S | 3 | NHCOC$_4$H$_9$ | l | | |
| 13 | NH | 1 | NHCOCH$_3$ | l | | |
| 14 | NCH$_3$ | 2 | N$_3$ | dl | | |
| 15 | NC$_4$H$_9$ | 2 | NHSOC$_3$H$_7$ | l | | |

EXAMPLE 16

Preparation of (l)-N-[3-(2,3-Dihydro-1-oxo-1H-inden-5-yl)-2-oxooxazolidin-5-ylmethyl]acetamide (I; R$_1$, R$_2$=O, X=CH$_2$, n=1, B=NHCOCH$_3$)

To a solution of chromium (VI) oxide (3.58 g, 35.8 mmol) in acetic acid (35 mL) and water (8.75 mL) was added compound (I) (R$_1$=R$_2$=H, X=CH$_2$, n=1, B=NHCOCH$_3$) (7 g, 25.5 mmol) in acetic acid (35 mL) and acetic anhydride (10.6 mL). The mixture was stirred at room temperature overnight and then extracted with methylene chloride three times after adding water. The combined organic layer was washed with saturated sodium bicarbonate, brine, and dried (MgSO$_4$). Removal of the solvent afforded the crude product which was purified by flash column chromatography to yield 2.55 g (35%) of (l)-N-[3-(2,3-dihydro-1-oxo-1H-inden-5-yl)-2-oxooxazolidin-5-ylmethyl]acetamide as a white solid. m.p. 163°–165° C.; IR (CHCl$_3$): 1759, 1699, 1608 cm$^{-1}$; NMR(CDCl$_3$) δ: 7.73 (d,1H), 7.67 (s,1H), 7.50 (d,1H), 6.43 (bs,1H), 4.83 (m,1H), 4.13 (t,1H), 3.88 (dd,1H), 3.70 (t,2H), 3.13 (t,2H), 2.70 (t,2H), 2.03 (s,3H); MS: m/z 288.1116 (M$^+$), calcd. for C$_{15}$H$_{16}$N$_2$O$_4$, 288.1110; [α]$_D$=−44° (C=1, CH$_3$CN).

EXAMPLE 17

Preparation of (l)-N-[3-(2,3-Dihydro-1-hydroxy-1H-inden-5-yl)-2-oxooxazolidin-5-ylmethyl]acetamide (I; R$_1$, R$_2$=H, OH, X=CH$_2$, n=1, B=NHCOCH$_3$)

To a solution of (l)-N-[3-(2,3-dihydro-1-oxo-1H-inden-5-yl)-2-oxooxazolidin-5-ylmethyl]acetamide (0.5 g, 1.73 mmol) in ethanol (10 mL) and THF (2 mL) was added sodium borohydride (265 mg, 6.94 mmol). The mixture was stirred at room temperature for three hours before quenching with 10% hydrochloric acid. Ethanol was removed, the residue was diluted with 10% hydrochloric acid and extracted with hot chloroform three times. The combined chloroform layer was washed with brine and dried ($Na_2SO_4$). Removal of the solvent gave the crude product which was purified by flash column chromatography to afford 385 mg (77%) of (l)-N-[3-(2,3-dihydro-1-hydroxy-1H-inden-5-yl)-2-oxooxazolidin-5-ylmethyl]acetamide as a white solid. m.p. 158°–159° C.; IR (nujol): 3286, 1737, 1653 $cm^{-1}$; NMR ($d_6$-DMSO) δ: 8.27 (bs,1H), 7.40 (s,1H), 7.33 (s,2H), 5.22 (bs,1H), 5.02 (bs,1H), 4.70 (m,1H), 4.10 (t,1H), 3.73 (t,1H), 3.40 (m,2H), 2.90 (m,1H), 2.72 (m,1H), 2.33 (m,1H), 1.83 (s,3H), 1.77 (m,1H); MS: m/z 290.1270 (M+), calcd. for $C_{15}H_{18}N_2O_4$, 290.1267; $[α]_D = -19°$ (C=1, $CH_3OH$).

EXAMPLE 18

Preparation of (l)-N-[3-[1,2-Dihydro-1-(4-methyl-1-piperazinylimino)-1H-inden-5-yl]-2-oxooxazolidin-5-ylmethyl]acetamide (I, $R_1$, 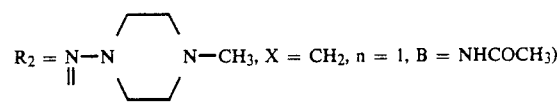 $R_2$ = N—N⏑N—CH_3, X = $CH_2$, n = 1, B = $NHCOCH_3$)

A mixture of (l)-N-[3-(2,3-dihydro-1-oxo-1H-inden-5-yl)-2-oxooxazolidin-5-ylmethyl]acetamide (0.2 g, 0.69 mmol) and 1-amino-4-methylpiperazine (120 mg, 1.04 mmol) in dioxane (5 mL) containing boron trifluoride etherate (0.05 mL) and 4 A molecular sieves was refluxed overnight. The solvent was removed and the residue was chromatographed to give 127 mg (48%) of the title compound. m.p. >200° C. (dec); NMR ($d_6$-DMSO) δ: 8.27 (bs,1H), 7.67–7.50 (m,3H), 4.73 (bs,1H), 4.13 (t,1H), 3.77 (t,1H), 3.40 (m,2H), 3.00 (m,2H), 2.80 (m,6H), 2.46 (bs,4H), 2.18 (s,3H), 1.83 (s,3H); MS: m/z 385.2107 (M+), calcd. for $C_{20}H_{27}N_5O_3$, 385.2114.

By using the procedures described in Examples 16–18, the following compounds in Table II were prepared or can be prepared.

TABLE II

| Ex. | X | n | $R_1,R_2$ | B | Isomer | m.p. (°C.) | [α]D |
|---|---|---|---|---|---|---|---|
| 16 | $CH_2$ | 1 | =O | $NHCOCH_3$ | l | 163–165 | −44° (C = 1, $CH_3CN$) |
| 17 | $CH_2$ | 1 | H,OH | $NHCOCH_3$ | l | 158–159 | −19° (C = 1, $CH_3OH$) |
| 18 | $CH_2$ | 1 | =N—N⏑N—CH_3 | $NHCOCH_3$ | l | >200° (dec) | |
| 19 | $CH_2$ | 1 | H,$NH_2$ | $NHCOCH_3$ | l | | |
| 20 | $CH_2$ | 1 | H,N(CH_3)_2 | $NHSOCH_3$ | l | | |
| 21 | $CH_2$ | 1 | =NOH | $NHCOCH_3$ | l | | |
| 22 | $CH_2$ | 2 | =$NOCH_3$ | $NH_2$ | l | | |
| 23 | $CH_2$ | 3 | =NOCOC_3H_7 | $N_3$ | l | | |
| 24 | O | 1 | =O | $NHCOCH_3$ | dl | | |
| 25 | O | 1 | H,OH | $NHCO_2CH_3$ | l | | |
| 26 | O | 2 | =O | $NHCOCH_3$ | l | | |
| 27 | O | 2 | =N—N⏑N—CH_3 | $NHSOC_2H_5$ | l | | |
| 28 | S | 1 | H,OH | NHCO-cyclopropyl | l | | |
| 29 | S | 3 | H,$NH_2$ | $N(CH_3)COCH_3$ | l | | |
| 30 | NH | 1 | =O | $NHCOCH_3$ | l | | |
| 31 | $NCH_3$ | 2 | H,OH | $NHSO_2CH_3$ | dl | | |

TABLE II-continued

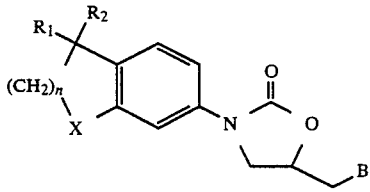

| Ex. | X | n | $R_1,R_2$ | B | Isomer | m.p. (°C.) | $[\alpha]D$ |
|---|---|---|---|---|---|---|---|
| 32 | $NC_4H_9$ | 2 | $=NOC_4H_9$ | $N_3$ | dl | | |

Dosage Forms

The antibacterial agents of this invention can be administered by any means that produces contact of the active agent with the agents' site of action in the body of a mammal. They can be administered by any conventional means available for use in conjunction with pharmaceuticals, either as individual therapeutic agents or in a combination of therapeutic agents. They can be administered alone, but are generally administered with a pharmaceutical carrier selected on the basis of the chosen route of administration and standard pharmaceutical practice.

The dosage administered will, of course, vary depending upon known factors such as the pharmacodynamic characteristics of the particular agent, and its mode and route of administration; age, health, and weight of the recipient; nature and extent of symptoms; kind of concurrent treatment; frequency of treatment; and the effect desired. Usually, a daily dosage of active ingredient can be about 5 to 20 milligrams per kilogram of body weight. Ordinarily, when the more potent compounds of this invention are used, 5 to 15, and preferably 5 to 7.5 milligrams per kilogram per day, given in divided oral doses 2 to 4 times a day or in sustained release form, is effective to obtain desired results. These drugs may also be administered parenterally.

Projected therapeutic levels in humans should be attained by the oral administration of 5–20 mg/kg of body weight given in divided doses two to four times daily. The dosages may be increased in severe or life-threatening infections.

Dosage forms (compositions) suitable for internal administration contain from about 1.0 milligram to about 500 milligrams of active ingredient per unit. In these pharmaceutical compositions, the active ingredient will ordinarily be present in an amount of about 0.5–95% by weight based on the total weight of the composition.

The active ingredient can be administered orally in solid dosage forms, such as capsules, tablets, and powders, or in liquid dosage forms, such as elixirs, syrups, and suspensions. It can also be administered parenterally, in sterile liquid dosage forms.

Gelatin capsules contain the active ingredient and powdered carriers, such as lactose, sucrose, manitol, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration contain preferably a water soluble salt of the active ingredient, suitable stabilizing agents, and, if necessary, buffer substances. Antiooxidants such as sodium bisulfate, sodium sulfite, or ascorbic acid either alone or combined are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences*, A. Osol, a standard reference text in this field.

Useful pharmaceutical dosage forms for administration of the compounds of this invention can be illustrated as follows:

Capsules

A large number of unit capsules are prepared by filling standard two-piece hard gelatin capsules each with 75 milligrams of powdered active ingredient, 150 milligrams of lactose, 24 milligrams of talc, and 6 milligrams of magnesium stearate.

Soft Gelatin Capsules

A mixture of active ingredient in soybean oil is prepared and injected by means of a positive displacement pump into gelatin to form soft gelatin capsules containing 75 milligrams of the active ingredient. The capsules are washed and dried.

Tablets

A large number of tablets are prepared by conventional procedures so that the dosage unit is 75 milligrams of active ingredient, 0.2 milligrams of colloidal silicon dioxide, 5 milligrams of magnesium stearate, 250 milligrams for microcrystalline cellulose, 11 milligrams of cornstarch and 98.8 milligrams of lactose. Appropriate coatings may be applied to increase palatability or delay absorption.

Injectables

A parenteral composition suitable for administration by injection is prepared by stirring 1.5% by weight of active ingredient in 10% by volume propylene glycol and water. The solution is made isotonic with sodium chloride and sterilized.

Suspensions

An aqueous suspension is prepared for oral administration so that each 5 milliliters contain 75 milligrams of finely-divided active ingredients. 200 milligrams of sodium carboxymethyl cellulose, 5 milligrams of sodium benzoate, 1.0 grams of sorbitol solution, U.S.P., and 0.025 milliliters of vanillin.

Utility

Test results indicate that the novel compounds of this invention are biologically active against gram positive bacteria including multiply antibiotic resistant strains of staphylococci and streptococci. These compounds are potentially useful for the treatment of both human and animal bacterial infections including diseases of the respiratory, gastrointestinal, genitourinary systems; blood; interstitial fluids; and soft tissues.

As shown in Table III, compounds of Formula (I) exert an in vitro antibacterial effect. A standard microdilution method (*National Committee for Clinical Standards*. Tentative standard M7-T. Standard methods for dilution antimicrobial susceptibility tests for bacteria that grow aerobically. National Committee for Clinical Laboratory Standards, Villanova, Pa. 1982) with Mueller-Hinton broth is used to determine the 24-hour minimal inhibitory concentrations (MIC's) for test strains of *Staphylococcus aureus* and *Escherichia coli*.

The in vivo potency of these compounds is exemplified by the data summarized in Table IV. Determinations of in vivo efficacy are performed by inoculating mice intraperitoneally with cultures of the infecting organism diluted to produce 100% mortality in control animals within twenty-four hours. The culture of *S. aureus* used to infect the animals was diluted to the required bacterial density using 5% aqueous hog gastric mucin. The compounds are dissolved or suspended in 0.25% aqueous Methocel ® (Methocel ®: Hydroxypropyl Methylcellulose, E15 Premium, Dow Chemical Company) for oral administration or sterile distilled water containing 5% dimethylsulfoxide (Fisher Scientific Company, Fairlawn, N.J.) for subcutaneous administration. The mice are dosed at one hour and at four hours post-infection. Mortality is recorded daily until test termination seven days post infection. The number of survivors in each treatment group on the seventh day after infection is used in the calculation of the $ED_{50}$, the dose of compound that protects 50% of the mice (Litchfield, J. T. and Wildoxon. A simplified method for evaluating dose-effect experiments. *J. Pharmacol Exp. Ther.*, 96:99–113, 1949).

TABLE III

In Vitro Broth Microdilution Minimal Inhibitory Concentrations (MIC's)

| Ex. No. | Minimum Inhibitory Concentration (µg/mL) | |
| --- | --- | --- |
|  | *Staphylococcus aureus* | *Escherichia coli* |
| 1F | 2 | >128 |
| 16 | 2–4 | >128 |
| 17 | 8 | >128 |
| 18 | 8–16 | >128 |

TABLE IV

In Vivo Activity of Compounds Against *Staphylococcus aureus* in an Acute Lethal Mouse Model

| Ex. No. | $ED_{50}$ (mg/kg) | |
| --- | --- | --- |
|  | Oral Administration | Subcutaneous Administration |
| 1F | 2.2 | 1.7 |
| 16 | 1.6 | 1.2 |
| 17 | 1.9 | 1.8 |
| 18 | 13.9 | 20.3 |

What is claimed is:
1. A compound having the formula

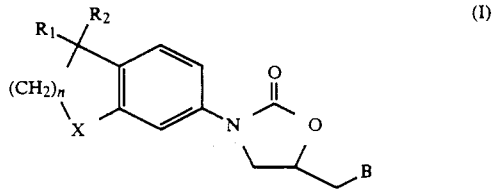

wherein for the l isomer or racemic mixtures containing it

B is $NH_2$,

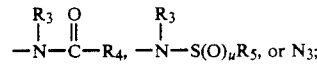

u is 1 or 2;
$R_3$ is H, alkyl of 1–10 carbon atoms, or cycloalkyl of 3–8 carbon atoms;
$R_4$ is H, alkyl of 1–4 carbon atoms, alkenyl of 2–4 carbon atoms, cycloalkyl of 3–4 carbon atoms, or $OR_5$;
$R_5$ is alkyl of 1–4 carbon atoms;
X is O or S;
$R_6$ is H or alkyl of 1–4 carbon atoms;
n is 1–3; and
$R_1$ and $R_2$ taken together are

or a pharmaceutically suitable salt thereof; provided that:
(1) when n is 2, then X is not S; and
(2) when n is 3, then X is not O.
2. A compound of claim 1 wherein B is

where $R_4$ is H, $CH_3$, or $OR_5$.
3. A compound of claim 1 wherein n is 1 or 2.
4. A compound of claim 1 wherein:
(a) B is

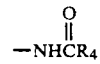

where $R_4$ is H, $CH_3$, or $OR_5$; and (b) n is 1 or 2.

5. A compound of claim 1 wherein B is

6. A compound of claim 5 wherein n is 1.

7. A pharmaceutical composition consisting essentially of a pharmaceutically suitable carrier and an antibacterial amount of a compound of claim 1.

8. A pharmaceutical composition consisting essentially of a pharmaceutically suitable carrier and an antibacterial amount of a compound of claim 2.

9. A pharmaceutical composition consisting essentially of a pharmaceutically suitable carrier and an antibacterial amount of a compound of claim 3.

10. A pharmaceutical composition consisting essentially of a pharmaceutically suitable carrier and an antibacterial amount of a compound of claim 4.

11. A pharmaceutical composition consisting essentially of a pharmaceutically suitable carrier and an antibacterial amount of a compound of claim 5.

12. A pharmaceutical composition consisting essentially of a pharmaceutically suitable carrier and an antibacterial amount of a compound of claim 6.

13. A method of treating a bacterial infection in a mammal comprising administering to the mammal an antibacterial amount of a compound of claim 1.

14. A method of treating a bacterial infection in a mammal comprising administering to the mammal an antibacterial amount of a compound of claim 2.

15. A method of treating a bacterial infection in a mammal comprising administering to the mammal an antibacterial amount of a compound of claim 3.

16. A method of treating a bacterial infection in a mammal comprising administering to the mammal an antibacterial amount of a compound of claim 4.

17. A method of treating a bacterial infection in a mammal comprising administering to the mammal an antibacterial amount of a compound of claim 5.

18. A method of treating a bacterial infection in a mammal comprising administering to the mammal an antibacterial amount of a compound of claim 6.

* * * * *